US009187390B2

(12) United States Patent
Murray et al.

(10) Patent No.: US 9,187,390 B2
(45) Date of Patent: Nov. 17, 2015

(54) LIGNIN CONVERSION PROCESS

(75) Inventors: Aaron Murray, Chardon, OH (US);
Steven Ryba, Wadsworth, OH (US)

(73) Assignee: Biochemtex S.p.A., Tortona (AL) (IT)

(*) Notice: Subject to any disclaimer, the term of this patent is extended or adjusted under 35 U.S.C. 154(b) by 25 days.

(21) Appl. No.: 14/124,028

(22) PCT Filed: Jun. 15, 2012

(86) PCT No.: PCT/US2012/042746
§ 371 (c)(1),
(2), (4) Date: Dec. 5, 2013

(87) PCT Pub. No.: WO2012/174429
PCT Pub. Date: Dec. 20, 2012

(65) Prior Publication Data
US 2014/0135470 A1 May 15, 2014

Related U.S. Application Data

(60) Provisional application No. 61/498,221, filed on Jun. 17, 2011.

(51) Int. Cl.
| C07C 1/22 | (2006.01) |
| C07C 29/156 | (2006.01) |
| C08G 63/78 | (2006.01) |
| C08G 63/183 | (2006.01) |
| C08H 7/00 | (2011.01) |
| C10G 1/08 | (2006.01) |
| D21C 3/00 | (2006.01) |
| C10G 1/06 | (2006.01) |

(52) U.S. Cl.
CPC ............... C07C 29/156 (2013.01); C07C 1/22 (2013.01); C08G 63/183 (2013.01); C08G 63/78 (2013.01); C08H 6/00 (2013.01); C10G 1/065 (2013.01); C10G 1/083 (2013.01); C10G 1/086 (2013.01); D21C 3/003 (2013.01); C10G 2300/1014 (2013.01); C10G 2300/805 (2013.01); Y02E 50/32 (2013.01)

(58) Field of Classification Search
CPC .......... C10G 1/06; C10G 1/065; C10G 1/083; C10G 1/086; C10G 2300/1014; C10G 2300/805; C07C 1/22; C07C 29/156; C08G 63/183; C08G 63/78; C08H 6/00; D21C 3/003; Y02E 50/32
USPC ....................................................... 568/799
See application file for complete search history.

(56) References Cited

U.S. PATENT DOCUMENTS

| 4,647,704 A * | 3/1987 | Engel et al. .................... 568/716 |
| 4,731,491 A | 3/1988 | Urban et al. |
| 5,006,496 A * | 4/1991 | Huizinga et al. ................ 502/61 |
| 5,959,167 A | 9/1999 | Shabtai et al. |
| 7,425,657 B1 * | 9/2008 | Elliott et al. .................... 568/667 |
| 2008/0050792 A1 | 2/2008 | Zmierczak et al. |
| 2010/0200531 A1 * | 8/2010 | Komiya et al. .................. 215/40 |

FOREIGN PATENT DOCUMENTS

| CN | 102040483 A | 5/2011 | |
| WO | WO2009155673 | * 12/2009 | |
| WO | 2011/061400 A1 | 5/2011 | |
| WO | 2011/117705 A2 | 9/2011 | |
| WO | WO2011/123897 | * 10/2011 | ............... C10G 1/06 |
| WO | 2012/174429 A1 | 12/2012 | |
| WO | 2013/011206 A1 | 1/2013 | |

OTHER PUBLICATIONS

Gupta, et al., "ZnO: a versatile agent for benzylic oxidations," Tetrahedron Letters 46, 4957-4960 (2005).*
Gross et al., "Determinations of Molecular Weight of Lignin Degradation Products by Three Methods," Analytical Chemistry, 30(4), 518-521, 1958.*
"KOV piston pumps with ball valves for high-pressure slurry pumping", Putzmeister, Jan. 1, 2010, pp. 47-1.
Parveen Kumar et al., "Methods for Pretreatment of Lignocellulosic Biomass for Efficient Hydrolysis and Biofuel Production", Industrial & Engineering Chemistry Research, Apr. 15, 2009, pp. 3713-3729, vol. 48, No. 8, American Chemical Society, US.
Xingyu Wang et al., "Exploiting H-transfer reactions with RANEY Ni for upgrade of phenolic and aromatic biorefinery feeds under unusual, low-severity conditions", Energy & Environmental Science, Jan. 1, 2012, p. 8244, vol. 5, No. 8.
Kirk D.F. et al., "Gravity Concentration", Kirk-Othmer Encyclopedia of Chemical Technology, Jan. 1, 1980, pp. 1-29, vol. 12, John Wiley & Sons, New York, U.S.
De Jongh & R P P Rijs J A, "Pump Design", Arakis, Mar. 1, 2004, pp. 1-45.

* cited by examiner

Primary Examiner — Paul A Zucker
Assistant Examiner — Mark Luderer
(74) Attorney, Agent, or Firm — Edwin A. Sisson, Attorney at Law, LLC

(57) ABSTRACT

This specification discloses a complete method to manufacture polyester articles from freshly harvested ligno-cellulosic biomass. The process steps include pretreating the biomass and the converting the lignin to one of several possible organic steams by deoxygenating and dehydrogenating the lignin in the presence of a Raney Nickel catalyst, separating the organics, and then processing the organics into polyester feedstocks and converting those feedstocks to polyester.

6 Claims, 4 Drawing Sheets

LIGNIN CONVERSION PROCESS

PRIORITY AND CROSS REFERENCES

This patent application claims priority from International Application No. PCT/US2012/042746, filed on 15 Jun. 2012, which claims priority from U.S. Provisional 61498221, filed on 17 Jun. 2011, the teachings of both of which are incorporated in their entirety.

BACKGROUND

There is a long history trying to convert lignin from lignocellulosic (lignocellulosic) biomass into useful components. Three categories of lignin isolation from biomass can be broadly classified.

The first is the Organosolv process which extracts the lignin with organic solvents and then treats the extracted lignin. The drawback of this process is the presence and use of organic solvents which must later be removed from the products.

The second is the various Kraft processes used in the paper and pulp industry. Kraft lignin has been extracted from the ligno-cellulosic biomass using acids and bases and thus requiring removal and neutralization of the excess acids and bases.

The third is the base depolymerization of the lignin, again attacking the lignin and leaving the base as a contaminant to deal with.

However, with the advent of second generation biomass facilities, the lignin containing by-product streams contain high amounts of water, cellulose, and lignin as opposed to the first generation facilities which relied upon purified starches from grains as the sugar(s) for fermentation, leaving very little lignin.

The second generation processes remove the sugars from the ligno-cellulosic polymers, in particular, the C6 sugars which are known to be harder to extract and convert to the respective oligomer and monomers. In any event, the second generation systems typically ferment the sugars in the presence of the lignin, with the lignin being present in a by-product stream with a high water content.

There exists therefore the need for a process to convert the lignin from second generation ligno-cellulosic biomass conversion process to usable compounds.

SUMMARY

Disclosed in this specification is a single step process for the conversion of a pre-treated lignin feedstream into a converted lignin stream. The process is comprised of combining in a lignin conversion vessel; the pre-treated lignin feedstream, water supplied from the group consisting of the pre-treated lignin feedstream, a source other than the pre-treated lignin feedstream and mixtures thereof, hydrogen having a hydrogen pressure which at 25° C. is within a specified hydrogen pressure range, and a first catalyst, and maintaining the combination in the lignin conversion vessel at a temperature in a specified temperature range for a time sufficient to create the converted lignin stream, wherein the pre-treated lignin feedstream comprises lignin and the converted lignin stream has a composition comprising of aromatic compounds (reformate) wherein the total area of the aromatic compounds (reformate) under a GC/MS curve of the converted lignin stream is within the range of about 60 to 95% of the total area under the GC/MS curve.

It is further disclosed that the first catalyst comprises an elemental metal catalyst which may include an elemental metal selected from the group consisting of Platinum, Palladium, Cesium, Copper, Nickel, Ruthenium, Rhodium, Gold, and Iridium. It is further disclosed that the first catalyst may be a bimetallic catalyst comprised of at least one metal selected from the group consisting of Platinum, Palladium, Cesium, Copper, Nickel, Ruthenium, Rhodium, and Gold. It is also disclosed that the first catalyst may be selected from the group consisting of Raney Nickel catalysts, Ruthenium containing catalysts, Palladium containing catalysts, Gold containing catalysts, Iridium containing catalysts and Platinum containing catalysts.

The weight of the first catalyst to the dry weight of the pre-treated lignin feedstream is disclosed as preferably being in a range selected from the group consisting of about 0.005 to about 2.0, of about 0.3 to about 1.5, and of about 0.75 to about 1.25.

An optional second catalyst is also disclosed which may be selected from the group consisting of a zeolite, solid acid catalyst, solid base catalyst or mixture of both.

It is further disclosed that the hydrogen pressure at 25° C. is in the range of 35 to 110 bar and the first temperature is in the range of 325° C. to 360° C.

It is further disclosed that depending upon the temperature and pressure selected, the converted lignin stream may have a composition selected from the group consisting of A) phenols wherein the total area of the phenols under a GC/MS curve of the converted lignin stream is within the range of about 45 to 95% of the total area under the GC/MS curve, B) cycloalkane alcohols wherein the total area of the cycloalkane alcohols under a GC/MS curve of the converted lignin stream is within the range of about 45 to 95% of the total area under the GC/MS curve, and C) naphthene rich naphtha compounds wherein the total area of the naphthene rich naphtha compounds under a GC/MS curve of the converted lignin stream is within the range of about 40 to 95% of the total area under the GC/MS curve.

Finally, it is disclosed that the product of the lignin conversion process can be used to manufacture a polyester bottle by A. Converting at least some of the compounds from the converted lignin stream to a phthalate selected from the group consisting of orthophthalic acid, isophthalic acid, terephthalic acid and their respective dimethyl esters, B. Producing a polyester polymer selected from the group consisting of polyethlene terephthalate derived from the terephthalate and copolyethylene terephthalates derived from the phthalate, C. Converting the polyester polymer into a polyester bottle.

DETAILED DESCRIPTION

Figure 1:
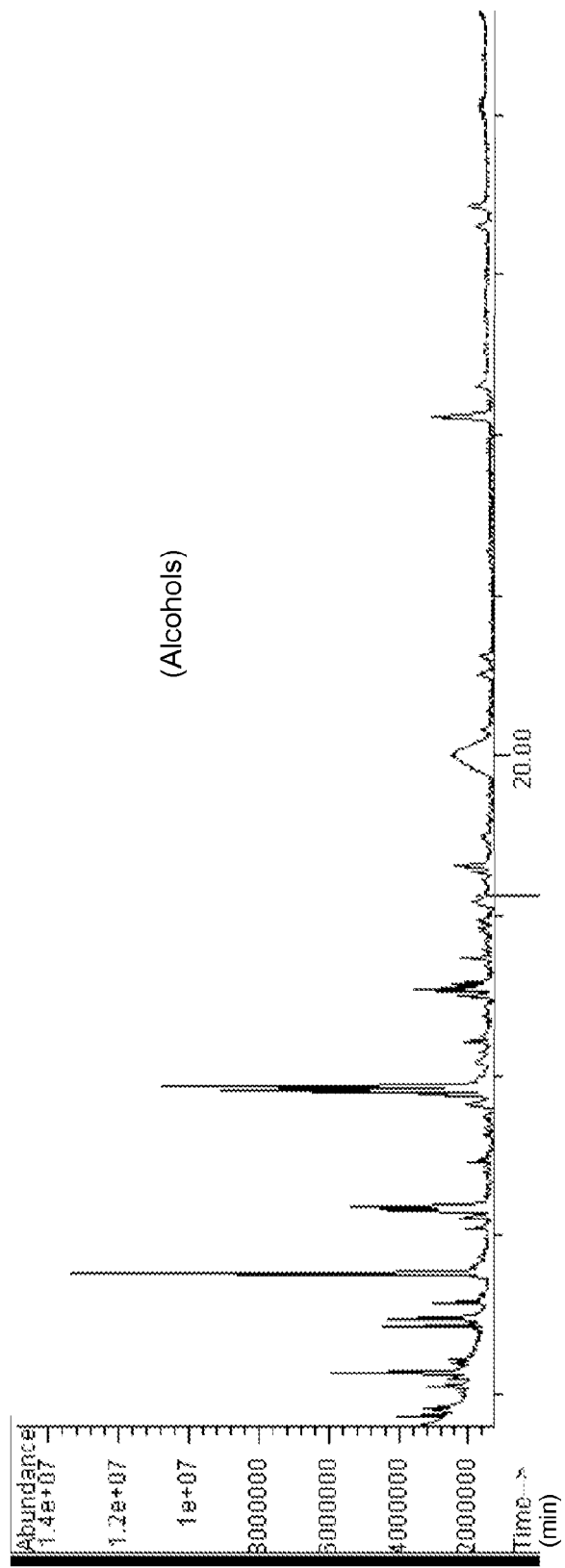
FIG. 1 is a gas chromatograph trace of a converted lignin stream comprising primarily alcohols.

Described in this specification is a complete process to produce a polyester article such as a container, like soft drink or beer bottles, useful for packaging food and beverages from ligno-cellulosic biomass. Disclosed is the integrated process starting from the freshly harvested untreated ligno-cellulosic biomass, pretreating the ligno-cellulosic biomass, fermenting some of the sugars derived from the ligno-cellulosic biomass to a product which was removed from the stream. The stream from which the fermented product was removed comprised primarily of water and lignin. The stream comprising water and lignin was passed to a lignin conversion vessel and the lignin converted to usable hydrocarbons, in particular benzene, toluene and mixed xylenes. These hydrocarbon species can be easily phase separated from water and further converted to phthalates, of which terephthalic acid or its dimethyl ester is of primary interest. The terephthalic acid or its dimethyl ester can then be reacted with ethylene glycol to make bottle grade polyester resin, which in turn can be manufactured into a bottle for soft drinks, beer, and other food and beverages.

I. Process Feedstock

The claimed process utilizes a feed or feedstock comprising lignin. It can also utilize a feedstock consisting of lignin, or a feedstock consisting essentially of lignin, or a feedstock comprising at least 95% lignin by dry weight.

Lignin does not have a single chemical structure. In fact, according to the Kirk Othmer Encyclopedia, the exact chemical structure of lignin, as it occurs in wood, is not known and because it is hard to extract from wood without changing its structure, the exact structure may never be known. While there are many variations of lignin, the term lignin, as used in this specification, refers to any polymer comprising p-hydroxyphenyl units, syringyl units, and guaiacyl units.

While pure lignin, such as Organosolv and Acetosolv lignins may be used, the extraction of lignin from its natural origins is expensive using organic solvents with the attendant environmental issues.

The first step is the selection of the agricultural feedstock. The lignin to be converted in this invention can be present as a feed or feedstock of natural ligno-cellulosic biomass comprising of at least one carbohydrate and lignin unit. Depending upon how the natural ligno-cellulosic biomass is treated another embodiment of the feedstock may have the composition and unique decomposition temperatures and surface areas as described below.

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the fraction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even more preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feedstock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barley, oats, brome-grass (*Bronnus*) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:
1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood useful in this process is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood useful for this process is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The feedstock comprising lignin can be naturally occurring ligno-cellulosic biomass that has been ground to small particles, or one which has been further processed. One process for creating the pre-treated lignin feedstock comprising lignin, comprises the following steps.

II. Pretreatment

The ligno-cellulosic biomass feedstock is pre-treated before subjecting at least a portion of the lignin in the ligno-cellulosic biomass feedstock to the lignin conversion step. The term pre-treated ligno-cellulosic biomass feedstock means that the ligno-cellulosic feedstock as found in nature has been treated to remove at least a portion of the sugars from the ligno-cellulosic biomass feedstock.

The pretreatment with acid or base to create kraft lignin which treats the feedstock with acid and creates additional sulphur in the lignin, or a preferred pre-treatment is described below. Because a complete, sufficiently enabling process from plant to polyester article has never been disclosed before, it is disclosed in detail below.

There are many pre-treatment steps and schemes. One pretreatment process is the Organosolv process.

The Organosolv process isolates the lignin for further processing by extracting the lignin from the feedstock into an organic solvent phase with the organic solvent being a mixture of water and usually ethanol. The resultant product is then pressed and filtered to reduce the water/solvent content of the lignin. The filtered/pressed material is then dried to reduce the moisture and solvent content even more to where the water content of the lignin stream is less than 20% by weight, with less than 10% by weight being a preferred content, with 5% water content and substantially void of water being the most preferred water contents of the lignin stream of the Organosolv pre-treatment processes. The organic solvent content is also reduced and while the lignin stream is preferably substantially void of water, typical solvent contents may be less than 10% by weight solvent and less than 5% by weight solvent of the lignin stream.

The extracted lignin is then passed on to the lignin convertor. While there is no reason to believe the Organosolv lignin could not be used in the current process, the organosolv process is not preferred as hydrocarbons made from lignin conversion must necessarily be separated from the solvent. In addition, the solvent must be recovered and handled carefully. Therefore, the preferred lignin stream entering the lignin conversion step is substantially solvent free, where substantially solvent free means less than 25% by weight solvent, preferably less than 20% by weight solvent, or even more preferably less than 10% by weight solvent, with less than 5% by weight solvent being one of the most preferred compositions with solvent free or void of any solvent being the most preferred.

The preferred lignin stream entering the lignin conversion step preferably contains water, or is wet, where wet means a water content greater than 10% by weight, or more preferably, greater than 20% by weight.

The kraft lignin process is found in the pulp and paper industry and provides a feedstock of lignin which has been sulfonated, or comprising sulfur. Sulfur is detrimental to catalysts, so while a kraft lignin where the concentration of sulfur on a dry basis immediately prior to adding the lignin to the reactor is greater than 105% of the sulfur concentration of the ligno-cellulosic biomass feedstock on a dry basis can be tolerated, it is preferable to keep the concentration of sulfur on a dry basis of the lignin stream immediately prior to adding the lignin stream to the lignin conversion step less than 125% of the sulfur concentration of the ligno-cellulosic biomass feedstock on a dry basis, with less than 115% more preferred, and less than 105% the most preferred. The same preferred values and constraints apply to species of nitrates, ammonia, chlorine, calcium, sodium and potassium. However, care must be taken to exclude the amount of the sulfur, nitrates, ammonia, chlorine, potassium and calcium ions which are added from any water added to the process. These natural occurring ions from process or makeup water are not detrimental. It is the ions from acid and base treatments which are harmful to the process later on.

In most fermentation facilities, pre-treatment stops at the hydrolysis or viscosity reduction step. For the purposes of this specification, pre-treatment includes those steps prior to exposure to hydrogen and the first catalyst. Therefore the pre-treatment step includes hydrolysis and fermentation steps.

The current pre-treatment strategies imply subjecting the ligno-cellulosic biomass material to temperatures between 110-250° C. for 1-60 min e.g.:

Hot water extraction

Multistage dilute acid hydrolysis, which removes dissolved material before inhibitory substances are formed Dilute acid hydrolyses at relatively low severity conditions Alkaline wet oxidation Steam explosion.

A preferred pretreatment of a naturally occurring ligno-cellulosic biomass includes soaking of the naturally occurring ligno-cellulosic biomass feedstock and a steam explosion of at least a part of the soaked naturally occurring ligno-cellulosic biomass feedstock.

The soaking may occur in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or a mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. There could also be a sequential soaking which has a low temperature soak prior to a high temperature soak. The temperature of the low temperature soak is in the range of 25 to 155° C. Although the time could be lengthy, such as up to but less than 48 hours, or less than 24 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO_4$, $NH_3$, in order to achieve higher performance later on in the process. However, it is preferred that acid, base or halogens not to be used anywhere in the process or pre-treatment. The feedstock is preferably void of added sulfur, halogens, or nitrogen. The amount of sulfur, if present, in the composition is in the range of 0 to 1% by dry weight of the total composition.

Additionally, the amount of total halogens, if present, are in the range of 0 to 1% by dry weight of the total composition. By keeping halogens from the feedstock, there are no halogens in the lignin conversion products. It is generally preferable that the whole process, including the lignin conversion portion after pre-treatment be conducted substantially acid free or base free, which means that any compounds added to the process do not change the pH by more than 2 units in either direction.

The first liquid is then passed to a separation step where the first liquid is separated from the soaked biomass. The liquid will not completely separate so that at least a portion of the liquid is separated, with preferably as much liquid as possible is separated in an economic time frame. The liquid from this separation step is known as the first liquid stream comprising the first liquid. The first liquid will be the liquid used in the soaking, generally water and the soluble species of the feedstock. These water soluble species are typically glucan, xylan, galactan, arabinan, glucolygomers, xyloolygomers, galactolygomers and arabinolygomers. The solid biomass is called the first solid stream as it contains most, if not all, of the solids which include lignin.

The separation of the liquid can again be done by known techniques and likely some which have yet to be invented. A preferred piece of equipment is a press, as a press will generate a liquid under high pressure.

The first solid stream is then steam exploded to create a steam exploded stream. Steam explosion is a well known technique in the biomass field and any of the systems available today and in the future are believed suitable for this step. The severity of the steam explosion is known in the literature as Ro, and is a function of time and temperature and is expressed as $$Ro = t \exp^{[(T-100)/14.75]}$$

with temperature, T expressed in Celsius and time, t, expressed in common units.

The formula is also expressed as Log(Ro), namely $$Log(Ro) = Ln(t) + [(T-100)/14.75].$$

As disclosed in the operating conditions below, this process will produce a solids composition under a high Ro, and that is novel in its low furfural content. As shown in the data, furfural is not a naturally occurring compound in biomass. Furfural is made when the biomass is exposed to high temperatures.

Log(Ro) is preferably in the ranges of 2.8 to 5.3, 3 to 5.3, 3 to 5.0 and 3 to 4.3.

The steam exploded stream may be optionally washed at least with water and there may be other additives used as well. It is conceivable that another liquid may be used in the future, so water is not believed to be absolutely essential. At this point, water is the preferred liquid and if water is used, it is considered the third liquid. The liquid effluent from the optional wash is the third liquid stream. This wash step is not considered essential and is optional.

The washed steam exploded stream is then processed to remove at least a portion of the liquid in the washed steam exploded material. This separation step is also optional. The term at least a portion is removed, is to remind one that while removal of as much liquid as possible is desirable (pressing), it is unlikely that 100% removal is possible. In any event, 100% removal of the water is not desirable since water is needed for the subsequent hydrolysis reaction. The preferred process for this step is again a press, but other known techniques and those not invented yet are believed to be suitable. The solids separated from this process are in the second solid stream.

The liquid of the first liquid stream can then optionally be combined with the solids of the second solid stream.

The composition of the stream at this point can be characterized on the basis of their C5, C6 and furfural amounts. To avoid dilution effects, the expression of the ratio C5's/C6's and furfural to the C5's plus C6's, with furfural being present is sufficient to characterize the new compositions.

The total C5's in the composition is the sum of arabinan and xylan in the composition which includes the monomers, dimers, oligomers and polymers of arabinose and xylose in the liquid and solid of the composition. The total C6's in the composition is the glucan content which includes the monomers, dimers, oligomers and polymers in the liquid and solid.

As known in the literature, a typical steam exploded biomass will have a ratio of furfural to [C5's plus C6's]×10000 of at least 50, with a ratio of C5's to C6's greater than 0.55. The process described herein is capable of producing a steam exploded product with a furfural content greater than 0, that is furfural is always present, but having a ratio of furfural to (C5's plus C6's)×10000 of less than 60. Therefore a composition having a ratio of C5's to C6's in the range of 0.45 to 0.54, and a ratio of furfural to [C5's plus C6's]×10000 between 0 and 60, or more preferably 0 and 50, or more preferably between 0 and 30 is contemplated.

These compositions from the steam explosion can be characterized as always having furfural and having the ratio of C5's to C6's less than 0.45 and a ratio of furfural to C5's plus C6's×10000 of less than 40, or more preferably, a ratio of C5's to C6's less than 0.45 and a ratio of furfural to C5's plus C6's×10000 of less than 15, or more preferably the ratio of C5's to C6's less than 0.45 and a ratio of furfural to C5's plus C6's×10000 of less than 10; or more preferably a ratio of C5's to C6's less than 0.40 and a ratio of furfural to C5's plus C6's×10000 of less than 40, or even more preferably a ratio of C5's to C6's less than 0.40 and a ratio of furfural to C5's plus C6's×10000 of less than 9, the ratio of C5's to C6's less than 0.35 and a ratio of furfural to C5's plus C6's×10000 of less than 10, or even more preferably, the ratio of C5's to C6's less than 0.30 and a ratio of furfural to C5's plus C6's×10000 of less than 7.

The composition of the liquid stream can be described as always having furfural and having a ratio of C5's to C6's greater than 4.0 and a ratio of furfural to C5's plus C6's× 10000 of less than 80, or more preferably a ratio of C5's to C6's greater than 4.0 and a ratio of furfural to C5's plus C6's×10000 of less than 60, or even more preferably a ratio of C5's to C6's greater than 4.0 and a ratio of furfural to C5's plus C6's×10000 of less than 30, or a broader range of a ratio of C5's to C6's greater than 3.0 and a ratio of furfural to C5's plus C6's×10000 of less than 160.

Also contemplated is the composition of the liquid stream always having furfural and having a ratio of C5's to C6's greater than 1.0 and a ratio of furfural to C5's plus C6's×10000 of less than 800, or more preferably a ratio of C5's to C6's greater than 1.0 and a ratio of furfural to C5's plus C6's×10000 of less than 700, or even more preferably a ratio of C5's to C6's greater than 1.0 and a ratio of furfural to C5's plus C6's×10000 of less than 400, or the narrower broad range of a ratio of C5's to C6's greater than 1.0 and a ratio of furfural to C5's plus C6's×10000 of less than 300.

A preferred variation of the pre-treatment step is for the soaking step to be comprised of several soaking steps at different temperatures and times. The lignocellulosic biomass having a cellulose content of at least 5% by weight of the dry matter, and preferably at least 10% by weight of the dry matter of the biomass into a soaking zone or reactor, and introduce a vapor, usually steam and maintaining the biomass at a temperature for a set amount of time. Steam is added to the soaking reactor at an exemplary rate of 0.5 kg steam/1 kg biomass feedstock to 10 kg steam/1 kg biomass feedstock, depending upon the severity chosen. Instead of adding steam, liquid water can be added and heated up to those conditions. The soaking zone holds the biomass in the presence of steam and water for approximately 30 minutes to 3 hours or longer, again depending upon the severity desired. The soaking temperature can be in the range 100° C. to 210° C., or even higher, but with diminishing returns. After soaking, the solids/liquid/steam mixture is discharged into an inclined reactor, at typically the same pressure of the soaking reactor. At this point liquid is removed via a discharge screw and into the inclined reactor. The solid biomass is carried up the inclined reactor with the cooled condensate or even added water flowing countercurrent to the solid flow and removing free liquid with dissolved xylans and xylan derivatives.

Consider three soaking zones, A, B, and C respectively. The soaking zones A, B, and C are oriented in series. They are maintained at their respective temperature. In the case of Zone A, the steam entering the soaking zone A is at a Temperature $T_1$ and Pressure $P_1$, with biomass being kept in the zone at temperature $T_A$ and for a time, $t_A$. The biomass moves through a discharge screw, $A_d$, flowing into an inclined reactor ($A_i$) with liquid $L_A$ being removed.

The ligno-cellulosic biomass, which has been soaked once, moves into the next soaking zone, Zone B, being characterized similarly as Zone A. In the case of Zone B, the steam entering the soaking zone B is at a Temperature $T_2$ and Pressure $P_2$, with biomass being kept in the zone at temperature $T_B$ and for a time, $t_B$. The biomass moves through a discharge screw, $B_d$, flowing into an inclined reactor ($B_i$) with liquid $L_B$ being removed.

The biomass, now soaked and washed for the second time, is sent to a third soaking zone, Zone C, being characterized similarly as Zones A and B. In the case of Zone C, the steam entering the soaking zone C is at a Temperature $T_3$ and Pressure $P_3$, with biomass being kept in the zone at temperature $T_C$ and for a time, $t_C$. The biomass moves through a discharge screw, $C_d$, flowing into an inclined reactor ($C_i$) with liquid $L_C$ being removed.

The biomass is then moved to a compressor to prepare it for steam explosion. The last zone is to have its severity higher than the severity of at least one of the zones before it in the process.

The process could also be done in a single vertical reactor comprised of zones, such as those described in US 2008/0295981, (See FIG. 1 of US 2008/0295981).

The adaption to the vertical column is readily apparent once one of ordinary skill realizes that multiple washes in progressive temperature is beneficial. The biomass is fed into the top of the vessel passing into Zone A, where the biomass is treated at mild temperature conditions in the presence of steam introduced at temperature $T_1$ and pressure $P_1$ and biomass held at temperature $T_A$ for a set period of time $t_A$, having generally a low severity. The liquid, $L_A$, containing xylan can be separated from the biomass using an extraction screen indicated by the diagonal lines underneath Zone A or some other device and the solids passed into the next Zone, Zone B.

The flow could pass upward or downward depending upon the desired pattern.

In Zone B the biomass is treated in the presence of steam introduced at temperature $T_2$ and pressure $P_2$ and biomass held at temperature $T_B$ for a set period of time $t_B$, and the liquid, $L_B$, containing xylan is separated from the biomass using an extraction screen indicated by the diagonal lines underneath Zone B or some other device and the solids passed into the next Zone, Zone C.

In Zone C the biomass is treated in the presence of steam introduced at temperature $T_3$ and pressure $P_3$ and biomass held at temperature $T_C$ for a set period of time, $t_C$, and the liquid, $L_C$, containing xylan can be separated from the biomass using an extraction screen indicated by the diagonal lines underneath Zone C or some other device and the solids passed into the next Zone, or in this case, the compression step in preparation for steam explosion.

It is preferred to have the severity increase with each soaking.

After the washing steps are completed, the liquid streams can be collected and further treated. The solid biomass is then recovered and usually passed onto a steam explosion step, which could be mounted at the bottom of the vertical reactor.

In the above embodiment, the material flow is downward. However, the flow could also be upward with the liquid extraction device different so that the liquid, usually water, moves countercurrent to the flow of the biomass. The zones can be configured horizontal to each other and the biomass would thus move sideways.

The pre-treatment process may run as a continuous process or batch process.

It should be apparent from the above description that the pre-treatment is not limited to the embodiments as many variations of the pre-treatment as described are possible.

After pretreatment, the amount of solids by total weight of the compositions can be in any of the ranges of 3 to 85%, 3 to 65%, 3 to 20%, 11 to 99%; 14 to 99%; 16 to 99%; 19 to 99%; 21 to 99%; 24 to 99%; 26 to 99%; 29 to 99%; 31 to 99%; 36 to 99%; and 41 to 99%. This can alternatively be expressed as a minimum dry content, i.e. as a weight percent of the dry content relative to the water in the feedstock stream. This would correspond to at least 20 weight percent dry content, preferably at least 25 weight percent dry content, more preferably at least 30 weight percent dry content, and most preferably at least 40 weight percent dry content. The upper limit of these contents is by definition 100%, but in practice 80 weight percent would be the upper limit to these contents if they were expressed in ranges.

After the steam explosion, the stream containing the majority of the lignin and solids will be subjected to a hydrolysis or viscosity reduction step. The preferred hydrolysis is enzymatic hydrolysis where the stream containing the majority of the lignin and solids is exposed to enzymes at a temperature and pressure where the enzymes will convert the cellulosic compounds to their oligomeric and monomeric C5 and C6 sugars.

The steam exploded stream is then subjected to hydrolysis to create a hydrolyzed stream. Optionally at least a part of the liquid of the first liquid stream is added to the steam exploded stream. Also, water is optionally added. Hydrolysis of the steam exploded stream is realized by contacting the steam exploded stream with a catalyst. Enzymes and enzyme composition is the preferred catalyst. While laccase, an enzyme known to alter lignin, may be used, the composition is preferably void of at least one enzyme which converts lignin. A preferred hydrolysis of the steam exploded stream comprises the step of:

A) Contacting the steam exploded stream with at least a portion of a solvent, the solvent comprised of water soluble hydrolyzed species; wherein at least some of the water soluble hydrolyzed species are the same as the water soluble hydrolyzed species obtainable from the hydrolysis of the steam exploded stream;

B) Maintaining the contact between the steam exploded stream and the solvent at a temperature in the range of 20° C. to 200° C. for a time in the range of 5 minutes to 72 hours to create a hydrolyzed stream from the steam exploded stream.

The hydrolyzed stream can be comprised of carbohydrate monomers selected from the group consisting of glucose, xylose, and mannose.

The hydrolyzed stream can be subjected to fermentation to create a fermented stream comprised of the composition and water. The fermentation is performed by means of addition of yeast or yeast composition to the hydrolyzed stream.

Hydrolysis and fermentation can also be performed simultaneously, according to the well known technique of simultaneous saccharification and fermentation (SSF).

The composition derived from naturally occurring ligno-cellulosic biomass can be separated from the water in the fermented stream. The separation of the liquid can be done by known techniques and likely some which have yet to be invented. A preferred piece of equipment is a press.

The composition at this point is different from naturally occurring ligno-cellulosic biomass in that it has a large surface area as calculated according to the standard Brunauer, Emmett and Teller (BET) method.

The BET surface area of the dry composition of the pre-treated lignin feedstream is at least 4 m$^2$/gm more preferably in the range of 4 to 80 m$^2$/gm, with 4 to 50 m$^2$/gm being more preferable, 4 to 25 m$^2$/gm being even more preferred, and 4 to 15 m$^2$/gm being even more preferred and 4 to 12 m$^2$/gm being the most preferred.

The pre-treated lignin feedstream can be further characterized by the peaks generated during a thermal gravimetric analysis, known as TGA.

In thermogravimetric analysis, the plot of the weight with respect to temperature and the plot of the first derivative of weight with respect to temperature are commonly used.

If the decomposition of the material or of a component of the material occurs in a specific range of temperature, the plot of the first derivative of weight with respect to temperature presents a maximum in the specific range of temperature, defined also as first derivative peak. The value of temperature corresponding to the first derivative peak is considered the decomposition temperature of the material or of that component of the material.

The material is a composition of many components, which decompose in different specific temperature ranges, the plot of the first derivative of weight with respect to temperature presents first derivative peaks associated to the decomposition of each component in each specific temperature range.

The temperature values corresponding to the first derivative peaks are considered the decomposition temperatures of each component of the material.

As a general rule, a maximum is located between two minima. The values of temperature corresponding to the minima are considered as the initial decomposition temperature and the final decomposition temperature of the decomposition temperature range of the component whose decomposition temperature corresponds to the first derivative peak comprised between the two minima. In this way, a derivative peak corresponds to decomposition temperature range. The weight loss of the material in the range between the initial decomposition temperature and the final decomposition temperature is associated to the decomposition of that component of the material and to the first derivative peak.

Should the naturally occurring ligno-cellulosic biomass used to derive the lignin composition be a mixture of different species of grasses or plants or other materials, then the mixture of the naturally occurring ligno-cellulosic biomass is what should be used for the comparison with the material from which the composition was derived.

The pre-treated lignin feedstream created has the characteristics that temperature corresponding to the maximum value of the first lignin decomposition peak is less than the temperature corresponding to the maximum value of the first lignin decomposition peak of the naturally occurring ligno-cellulosic biomass. This difference is marked with the maximum value of the first lignin decomposition peak being less than the temperature corresponding to the maximum value of the first lignin decomposition peak of the naturally occurring ligno-cellulosic biomass by a value selected from the group consisting of at least 10° C., at least 15° C., at least 20° C., and at least 25° C.

This reduction in the maximum value of the first lignin decomposition temperature can be compared to the maximum value of the first lignin decomposition temperature after pre-treatment.

Additionally, the absolute mass on a dry basis associated with the first lignin decomposition peak of the claimed lignin composition is greater than the absolute mass on a dry basis of the second lignin decomposition peak. While for *Arundo donax*, the absolute mass of the first decomposition temperature of the naturally occurring ligno-cellulosic biomass is greater than the absolute mass of the second decomposition temperature of the naturally occurring ligno-cellulosic biomass, this is not true for many ligno-cellulosic biomasses such as corn stover and wheat straw. However, after conversion, the lignin composition derived from these biomasses has a mass on a dry basis associated with the first lignin decomposition temperature that is greater than the mass on a dry basis associated with the second lignin decomposition temperature.

The pre-treated lignin feedstream can be further characterized by comparing the temperature associated with the maximum value of the first lignin decomposition range with the temperature associated with the maximum value of the first lignin decomposition range of the ligno-cellulosic biomass used to derive the feedstock.

The feedstock can also be further characterized by the relative amount of carbohydrates, which include glucans and xylans, present on a dry basis. The composition may have the amount of total carbohydrates present in the composition in the range of 10 to 60% of the dry weight of the composition, with 10 to 40% more preferred with 5 to 35% even most preferred. Provided, of course, that the amount of total lignin present in the composition is in the range of 30 to 80% of the dry weight of the composition and the weight percent of the carbohydrates plus the weight percent of the lignin is less than 100% of the dry weight of the feedstock.

Because the pre-treated lignin feedstream may vary with the starting material from which it is derived, the naturally occurring ligno-cellulosic biomass from which the feedstock is derived can be selected from the group consisting of the grasses, food crops and woods such a hardwoods and softwoods.

After the hydrolysis step which has converted polymeric sugars to the oligomeric and monomeric constituents, the lignin containing stream usually undergoes at least one fermentation step to convert the sugar species to at least one fermentation product and separating the at least one fermentation product from the lignin, usually done by distillation. The remaining by-product stream comprising primarily lignin and water is now the lignin feedstream which can now be subjected to the lignin conversion step.

The preferred pre-treated lignin feedstream after pretreatment (which usually includes hydrolysis and fermentation), immediately prior to the lignin conversion step will comprise lignin, cellulose and water. There may be additional sugars and hemicellulose, but preferably the C5 sugars are dramatically reduced and the C6 non-polymeric sugars have been dramatically reduced leaving lignin, cellulose and water. There may also be proteins present, such as those coming from spent enzymes, yeast, and other previous processing steps.

For example, if the C6 sugars have been converted to ethanol in a fermentation step, the pre-treated lignin feedstream will have been distilled and filtered, but some of the enzymes from hydrolysis and/or fermentation will still remain.

A typical 60 gm lignin feedstream will comprise 33 gms of dry matter, with 45% of that dry matter being carbohydrates, leaving approximately 18 grams of dry lignin. Since lignin is approximately 50% oxygen, a theoretical yield of approximately 9 gm of non-oxygenated hydrocarbons is possible.

The desired pH of the lignin feedstream is neutral, which is in one of the pH ranges of 5 to 9, 5.5 to 8.5 and 6 to 8.

III. Lignin Conversion Process and Products

The lignin conversion process is a one step process, but can be done in one or two vessels. Depending upon the process conditions, the lignin conversion process can produce streams having vastly unique different compositions.

Because the feedstream is derived from ligno-cellulosic biomass, the product stream (the converted lignin stream) will have relatively young carbon materials as described in the pretreatment section regarding ASTM D 6866-04. Therefore the amount of contemporary carbon in the converted lignin stream is preferred to be at least 75%, with 85% more preferred, 95% even preferred and at least 99% even more preferred and at least 100% the most preferred.

The process combines the pre-treated lignin feedstream comprising lignin, water supplied from the group consisting of the pre-treated lignin feedstream, a source other than the pre-treated lignin feedstream and mixtures thereof, hydrogen having a hydrogen pressure, and a first catalyst in a lignin conversion vessel, wherein the hydrogen pressure at 25° C. is within a specified hydrogen pressure range and maintaining the combination in the lignin conversion vessel at a temperature in a specified temperature range for a time sufficient to create the converted lignin stream.

The pre-treated lignin feedstream can be a slurry, but in any event the lignin is present at 25° C. as a solid. The pre-treated lignin feedstream may also contain water insoluble carbohydrates such as cellulose, which are also present as a solid at 25° C. The pre-treated lignin feedstream may also contain water, even though the pre-treated lignin feedstream is a solid.

The amount of water may be as high 80% by weight of the unslurried pre-treated feedstream.

As explained below, depending upon the hydrogen pressure at 25° C. and the temperature of the reaction, vastly different products can be produced.

As demonstrated in the experimental section, the lignin conversion can be carried out in one step where the first and second pressure ranges, the first and second temperature ranges, and the first and second catalyst are the same and the first and second time periods add to a total time period.

The first catalyst used in the reaction is preferably an elemental metal catalyst which can comprise at least one sponge elemental metal created by the Raney process as described and claimed in U.S. Pat. No. 1,628,190, the teachings of which are incorporated in their entirety. That process as claimed creates an alloy of at least a first metal and a second metal dissolves the second metal out of the first metal, leaving behind a finely divided elemental first metal with high surface area. This high surface area is often described as a sponge structure. The preferred first catalyst of the lignin conversion process is known as Raney Nickel, or where the finely divided elemental metal is nickel.

The catalyst may also be a metal selected from the group consisting of Platinum, Palladium, Cesium, Copper, Nickel, Ruthenium, Rhodium, Gold and Iridium. The catalyst may be present as a bimetallic catalyst comprised of at least two metals, wherein one of the metals is selected from the group consisting of Platinum, Palladium, Cesium, Copper, Nickel, Ruthenium, Rhodium, Gold and Iridium. The bimetallic catalyst may be present in the form of an alloy. The alloy may be present on a support or the alloy particles may be free. It is preferred that bimetallic catalyst comprise at least two metals selected from the group consisting of Platinum, Palladium, Cesium, Copper, Nickel, Ruthenium, Rhodium, Gold and Iridium.

The bimetallic catalyst may also comprise a plurality of supported metal particles wherein a portion, but not all, of the plurality of metal particles comprise a metal selected from the group consisting of Platinum, Palladium, Cesium, Copper, Nickel, Ruthenium, Rhodium, Gold and Iridium. Another preferred supported bimetallic catalyst comprises a plurality of supported metal particles wherein at least a portion of the supported metal particles are elemental particles of at least two metals selected from the group consisting of Platinum, Palladium, Cesium, Copper, Nickel, Ruthenium, Rhodium, Gold and Iridium.

The elemental particles may have varying shapes and sizes, with a high surface area to the particle mass, which higher surface areas and smaller particle sizes, including nano-particles being the most desired.

For the supported catalysts, the particle per se, but may be present as a coating on the support, depending upon how the metal is deposited onto the catalyst/surface.

The support may also provide acidic or basic sites in which the reaction can proceed.

The amount of the first catalyst can be expressed by the weight of the elemental metal, in this case, nickel, to the dry weight of the lignin feedstream, where the weight of the elemental nickel to the dry weight of the lignin feedstream should be in the range of about 0.25 to about 2.0, with the range of about 0.3 to about 1.5 being more preferred with at least about 0.5 being the most preferred.

There may be an optional second catalyst which can be any of the standard known hydrogenation catalysts, with the preferred second catalyst being the same as the first catalyst.

When the second catalyst is the same as the first catalyst, the amount of the second catalyst is the same as the amount of the first catalyst.

There is also the preferred introduction of a third catalyst, which is different from the first and second catalysts. The preferred third catalyst is a Zeolite creating heterogeneous sites for the reactions to progress in an acidic environment without adding an acid.

Due to the presence of water the process pressure will not be the pressure of the hydrogen as charged at atmospheric conditions. The process pressure will be the vapor pressure of the water at the operating temperature, plus the pressure of the hydrogen. The water in the lignin conversion vessel may come from free water, which is water added to the vessel, the water may come from water which is part of the pre-treated lignin feedstream or the water may come from both added water or water which is part of the pre-treated lignin feedstream.

Additionally, the catalyst may be present as a heterogenous catalysts, in the form of loose particles. The catalyst does not have to be a fixed bed or other fixed arrangement. It may be supported, but heterogeneous as well. The process is generally carried out without adding any strong acid or strong base, or any halogen compound which is not already present in the pre-treated lignin feedstream.

At least four unique converted lignin streams can be produced by the process. The converted lignin streams can be characterized by the percent area of the compound(s) under the GC/MS curve of the total converted lignin stream which are organic liquids at standard temperature and pressure. In other words, the organic liquid stream is processed via GC/MS and the compounds identified and the amount of area under the GC/MS curve determined. The organic liquid stream at standard temperature and pressure is referred to as the converted lignin stream.

To produce a converted lignin stream wherein the percent area of the total amount of phenols under the total area of the GC/MS curve of the converted lignin stream is within the range of about 45 to 95%, the lignin conversion process should be operated within the temperature range of about 245° C. to about 300° C., with about 275° C. to about 290° C. being a preferred range, for a time of about 0.05 hrs to about 3 hrs. The initial reactor pressure based upon the hydrogen pressure is 21.7 bar to 104.5 bar at 25° C. It has also been shown that the converted lignin stream under these conditions will have a total amount of toluene plus mixed xylenes less than about 10% of the area under the GC/MS curve of the converted lignin stream, with less than about 5% of the area under the GC/MS curve of the converted lignin stream possible, with the percent area of all the compounds under the GC/MS curve totaling 100%.

To produce a converted lignin stream wherein the percent area of the total area of cycloalkane alcohols under the GC/MS curve of the converted lignin stream is within the range of about 45 to 95%, the lignin conversion process should be operated within the temperature range of about 270° C. to about 335° C., with about 290° C. to about 315° C. being a preferred range, for a time of about 0.05 hrs to about 2 hrs. The initial charge to the reactor of hydrogen pressure is 104.5 bar to 173.3 bar. It has also been shown that the converted lignin stream made under these conditions will have a total amount of phenolic compounds less than about 30% of the area under the GC/MS curve of the converted lignin stream, with less than about 20% of the area under the GC/MS curve of the converted lignin stream possible, with the percent area of all the compounds under the GC/MS curve totaling 100%.

To produce a converted lignin stream wherein the percent area of the total aromatic compounds (reformate) under the GC/MS curve of the converted lignin stream is within the range of about 60 to 95%, the lignin conversion process should be operated within the temperature range of about 305° C. to about 375° C., with about 320° C. to about 360° C. being a preferred range, for a time of about 0.05 hrs to about 2 hrs. The initial charge to the reactor of hydrogen pressure is 35 bar to 138.9 bar. It has also been shown that the converted lignin stream made under these conditions will have a total amount of cycloalkane compounds of less than about 10% of the area under the GC/MS curve of the converted lignin stream, with less than about 5% of the area under the GC/MS curve of the converted lignin stream possible, with percent area of all the compounds under the GC/MS curve totaling 100%.

To produce a converted lignin stream wherein the percent area of the total naphthene rich naphtha compounds of the total area under the GC/MS curve of the converted lignin stream is within the range of about 40 to 95%, the lignin conversion process should be operated within the temperature range of about 290° C. to about 340° C., with about 305° C. to about 330° C. being a preferred range, for a time of about 0.25 hrs to about 2 hrs. The initial charge to the reactor of hydrogen pressure is 121.6 bar to 173.3 bar. It has also been shown that the converted lignin stream made under these conditions will have a total amount of phenolic compounds of less than about 30% of the area under the GC/MS curve of the converted lignin stream, with less than about 20% of the area under the GC/MS curve of the converted lignin stream possible, with the percent area of all the compounds under the GC/MS curve totaling 100%.

In all cases, the ratio of the number of moles of hydrogen charged to the reactor to the number of moles of the organics (lignin and carbohydrates) should be at least 0.5. The moles of organics (lignin and carbohydrates) is the number of repeating units found in the various structures in the feedstream. For example, cellulose is repeating units of glucose which has a molecular weight of approximately 180. The number of moles of cellulose therefore is the number of moles of the repeating unit of glucose in the cellulose. While 0.5 is a minimum preferred ratio, it is preferable that more hydrogen be used so that a ratio of at least 1.0 is more preferred, with a ratio of at least 2.0 being even more preferred with a ratio of at least 3.5 being most preferred.

The time of the conversion should be a time sufficient to complete the reaction to the desired products. Such a time is at least 0.05 hours being the minimal sufficient time, with at least 0.25 hours being preferred, with at least 1 hour being more preferred, with at least 1.5 hours being more preferred, with at least 2.5 hours being the most preferred.

Because the converted lignin stream is organic, it can easily be separated from the water with a solvent wash and the converted lignin stream further converted.

In the case of the high aromatic stream, the toluene and mixed xylenes can be converted to any of the phthalates, in particular terephthalic acid or its dimethyl ester. This can be done using known industrial processes based upon the fossil derived phthalates. In particular the well known transalkylation process is preferred. The phthalate can then be converted into a polyester resin. In particular the terephthalic acid or its dimethyl ester can be reacted with ethylene glycol in the liquid or melt phase and the resulting product polycondensed into a polyester polymer containing the moieties derived from the terephthalic acid or its dimethyl ester. The polyester polymer can then be injection molded into a preform and subsequently reheated and blown into polyester bottles for food, soft drinks, or other beverages and packaged goods.

It has also been discovered that the process when conducted at low hydrogen pressures will actually produce hydrogen from the decomposition of the pre-treated lignin feedstock. It is believed that this phenomenon is due to the presence of carbohydrates, therefore the pre-treated lignin feedstock may also comprise sugars, which can be carbohydrates, cellulose, hemi-cellulose or simple sugars such as glucose, xylose and/or arabinose.

EXPERIMENTAL

I. Lignin Feedstream Preparation

The pre-treated lignin feedstream was prepared from *Arundo donax* as a starting ligno-cellulosic biomass. The ligno-cellulosic biomass was subjected to a pre-treatment according to the following procedure:

ligno-cellulosic biomass was introduced into a continuous reactor and subjected to a soaking treatment at 155° C. for 155 minutes. The soaked mixture was separated in a soaked liquid containing sugars from the ligno-cellulosic biomass and a fraction containing the solid soaked raw material by means of a press. The fraction containing the solid soaked raw material was subjected to steam explosion at 195° C. for 4 minutes. Steam exploded products were separated into a steam explosion liquid and a steam exploded solid.

Steam exploded solid was mixed with water to obtain a mixture having 7.5% dry matter content and the mixture was inserted into an enzymatic hydrolysis reactor. An enzyme cocktail was added, corresponding to concentration of 15 mg of protein per gram of glucans contained in the steam exploded solid. pH was corrected to 5 by adding KOH and enzymatic hydrolysis was carried out at 60° C. for 72 hours under agitation, producing the hydrolyzate, which is still a pre-treated lignin feedstream.

The hydrolyzate was inserted into a bioreactor with 3 g/l urea and 0.5 g/l of a fermenting yeast. pH was set to 5 and temperature to 30° C. and fermentation carried out for 48 hours. The fermentation broth, comprising solids, ethanol and other liquid fractions, was pressed by a press filtering at a temperature of 80° C. at 15 bar, for separating ethanol and liquid components from the solid-rich fraction. The solid-rich fraction extracted from the press, having a dry matter of 55%, was the pre-treated lignin feedstream used in the conversion experiments.

II. Compositions

Compositions by weight percent on a dry basis of the starting ligno-cellulosic biomass and lignin feedstream are reported in table 1. The lignin feedstream comprises lignin, complex sugars (insoluble glucans and insoluble xylans which have not been solubilized), ashes and other compounds. Compositions were determined according to standard analytical methods listed at the end of experimental section.

TABLE 1

Compositions of the starting ligno-cellulosic biomass and pre-treated lignin feedstream used in conversion experiments

|  | ligno-cellulosic biomass (dry weight %) | Pre-treated Lignin feedstream (dry weight %) |
|---|---|---|
| Lignin | 22.6 | 49.0 |
| Insoluble glucans | 37.5 | 30.6 |
| Insoluble xylans | 19.3 | 4.9 |
| Ash | 6.3 | 8.2 |
| Other compounds | 14.3 | 7.3 |

III. Conversion Procedure

The pre-treated lignin feedstream and sufficient water from a source other than the pre-treated lignin feedstream to reach a dry matter concentration of 20% were inserted in a 500 mL autoclave (the lignin conversion vessel); the autoclave was equipped with an internal thermocouple, dual pitched bladed agitator, internal cooling coil and a dip tube. After catalyst insertion, the reactor was pressurized to about 15 bar with nitrogen, stirred for five minutes, and vented. The purging cycle was repeated two more times and then two times with hydrogen. Finally, the reactor was pressurized at 25° C. to the desired hydrogen pressure and then heated with an electric heating mantle to the reaction temperature. Once the internal temperature of the reactor was stabilized, the reactor was stirred for the reaction time. Once the reaction time was completed, the heating mantle was removed and the cooling water turned on through the cooling coil. In about 30 minutes the internal temperature would fall below 40° C. and the reaction pressure was slowly vented for more than 20 minutes.

Two types of Nickel catalysts, Johnson Mathey A-5000 sponge nickel and Grace Davison's RaNI 6800, were used in the experiments and it was verified that similar results are obtained.

IV. Reaction Products Determination

The reactor contents were transferred to a Buchner filter, with paper of size Whatman #1, 11 microns, to remove the catalyst from the solution. The reaction products were extracted with methylene chloride.

GC/MS was used to analyze the converted lignin stream, by means of an Agilent 7890 gas chromatogram and an Agilent 5975 mass detector. Two different procedures were used. Procedure N. 1

A chromatography column RXI-5Sil MS, 30 meter, 0.25 mmID, 0.5 um df Cat#13638 was used with Helium flow of 1.3 ml/min 2 µl of solution of the reaction products and the solvent were heated to 150° C. (thermal ramp: 50° C. hold for 1 minute, to 130° C. at 6° C./min, hold 10 minutes at 130° C., to 150° C. at 6° C./min, hold 10 minutes at 150° C.) and injected into the chromatography column. The inlet of column injector was at a temperature of 300° C. and at a pressure of 1.062 bar. Total helium flow was 31.6 ml/min and a split of 10:1 was used. The split flow was 26 ml/min. The septum purge was 3 ml/min.

The MSD transfer line was at temperature of 280° C. for the entire run and the column transfer line was a HP-101 methyl siloxane-101 methyl siloxane (dimensions 12 m×200 µm×0.25 µm).

The mass detector (Transfer line at 280° C., MS source at 230° C., MS quad at 150° C.) was used for identifying reaction products in the range of 10-350 mass by means of ion fragmentation, EM voltage of 1871, Threshold of 25.

The detector parameters were 350° C., 45 ml/min hydrogen flow, 450 ml/min Air flow, and 26.729 ml/min.

A FID detector (detector temperature: 350° C.) was used for quantify reaction products by means of flame ionization.

Procedure N.1 was used for identifying aromatics, alcohols, and naphthenic compounds and is to be used for determining the amounts of the aromatics, alcohols, and naphthenic compounds in the converted lignin stream based upon the area under the GC curve.

Procedure N.2

A chromatographic column Restek Rxi-624Sil MS, 30 meter, 0.25 mm ID, 1.4 um df was used at a He flow of 4.0 ml/min.

2 μl of solution of the reaction products and the solvent were heated to 300° C. (thermal ramp: 50° C. hold for 1 minute, to 240° C. hold for 0 minutes, at 12° C./min, to 300° C. at 30° C./min, hold 17 minutes) and pulse injected into the chromatography column at an injection pulsed pressure of 3.5 bar for 30 seconds.

The pressure pulse modes of the GC increase inlet pressure just before the beginning of a run and return it to the normal value after a specified amount of time. The pressure pulse sweeps the sample out of the inlet and into the column faster, reducing the chance for sample decomposition in the inlet.

The inlet of the column injector was at a temperature of 220° C. and at a pressure of 1.70 bar. Total helium flow was 40 ml/min and the split was 10:1. A septum purge (flow 3 ml/min) was used.

The MSD transfer line was at temperature of 280° C. for the entire run and the column transfer line was a HP-101 methyl siloxane-101 methyl siloxane (dimensions 12 m×200 μm×0.25 μm).

The mass detector (MS source at 230° C., MS quad at 150° C.) was used at an EM voltage of 1941 V for identifying products in the range of 10-350 mass with a threshold of 25, FID detector was at a temperature of 310° C., with a $H_2$ flow of 45 ml/min, an air flow of 450 ml/min and a makeup flow of 26.7 ml/min.

Procedure N.2 was used for identifying phenolic compounds and is to be used for determining the amounts of the phenoloic compounds in the converted lignin stream based upon the area under the GC curve.

In the following examples, the reaction products in the converted lignin stream are listed in descending order with respect to the corresponding area in the GC/MS chromatogram. The area is given in percent with respect to the total area. Corresponding retention time is also reported. Not listed compounds are present in minor amount. The listed compounds account for more than about 70% by area of the whole converted lignin stream.

Example 1

Need of Ligno-Cellulosic Biomass Pretreatment 5.56 grams of ligno-cellulosic biomass which had not been pre-treated were reacted in the presence of 10 grams of water, 6.0 grams of Johnson Mathey A-5000 sponge nickel catalyst (50% by weight water/50% by weight catalyst). The reactor was pressurized to a hydrogen pressure of 77.5 bar at 25° C. Reaction temperature was 350° C., corresponding to an operating pressure in the range of 170-200 bar; reaction time was 1.5 hours. Reaction products were determined according to Procedure N.1. The resulting reaction products contained little or no hydrocarbons with a significant amount of unconverted solids. Thus, the need for a pre-treatment is established.

Example 2

Conversion of Lignin Feedstream to Phenols-Rich Converted Lignin Stream 5 grams of ~50% wet lignin feedstream were reacted in the presence of 18.00 grams of water, 1.20 grams of Johnson Mathey A-5000 sponge nickel catalyst (50% by weight water/50% by weight catalyst). The reactor was pressured to a hydrogen pressure of 13.8 bar at 25° C. Reaction temperature was 305° C., corresponding to an operating pressure in the range of 89-93 bar; reaction time was 1.0 hours.

Figure 4:
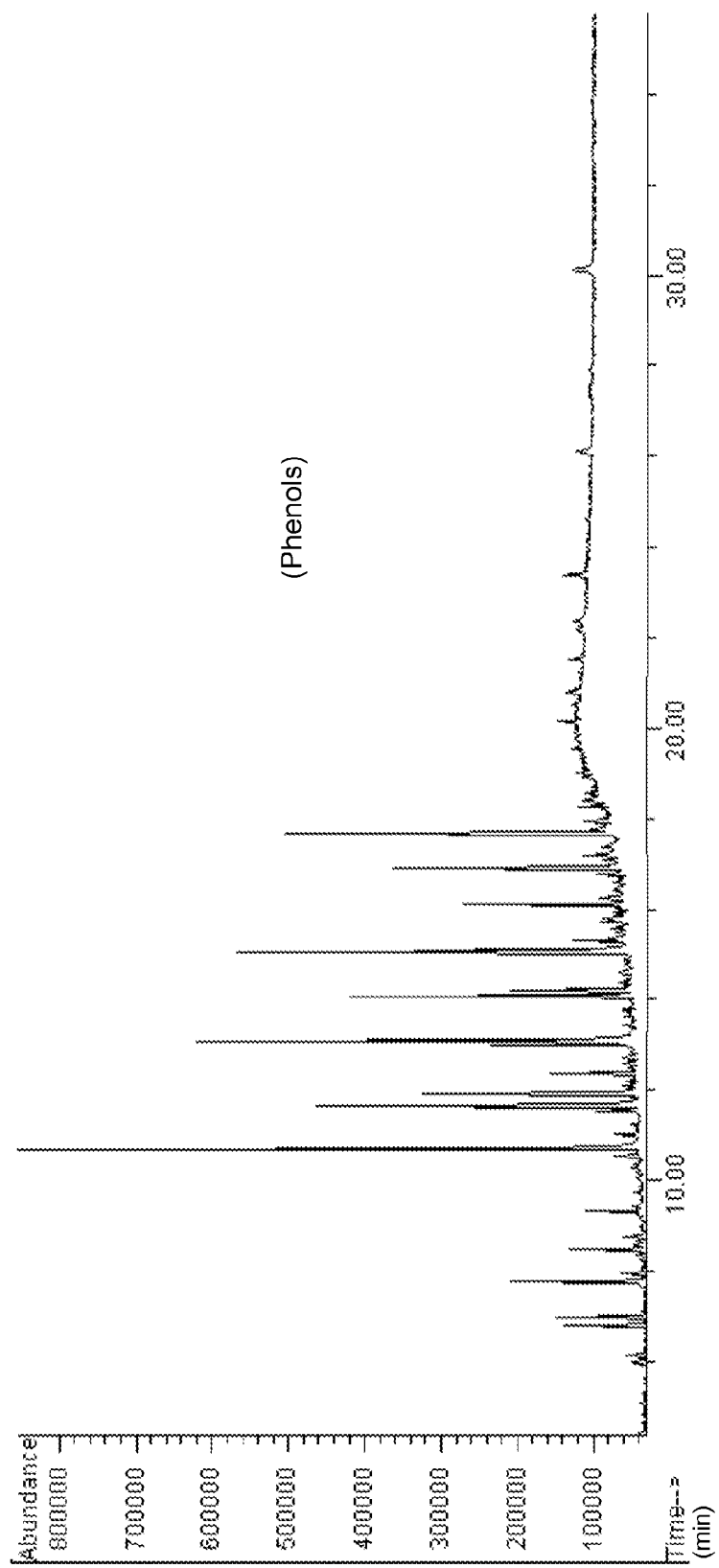
FIG. 4 is a gas chromatograph trace of a converted lignin stream comprising primarily phenols.

Reaction products were determined according to Procedure N.2. Composition of reaction products are reported in Table 2. Phenolic compounds are the major components of the converted lignin feedstream. A sample trace of this converted lignin stream is shown in FIG. 4.

TABLE 2

Composition of the phenols-rich converted lignin stream.

| Retention Time (min) | Area % | Compounds |
| --- | --- | --- |
| 10.7 | 10.07 | Phenol |
| 13.1 | 9.32 | Ethyl phenol |
| 15.0 | 6.80 | 2,6-Dimethoxy phenol |
| 11.7 | 6.07 | 2-Methoxyphenol |
| 17.7 | 5.62 | 2,6-Dimethoxy 4-propyl phenol |
| 11.9 | 5.44 | 4-Methylphenol |
| 14.1 | 4.99 | 2-Methoxy,4-ethyl phenol |
| 16.9 | 4.13 | 2,6-Dimethoxy 4-ethyl phenol |
| 15.1 | 3.11 | 2-Methoxy 4-propyl phenol |
| 16.1 | 2.88 | 2,6-Dimethoxy 4-methyl phenol |
| 7.8 | 2.81 | 2-Methylcyclopentanone |
| 13.0 | 2.62 | 2-Methoxy,4-methyl phenol |
| 14.2 | 2.23 | 4-Propyl phenol |
| 30.1 | 1.62 | >C15 alkane |
| 7.0 | 1.58 | Cyclopentanone |
| 12.4 | 1.50 | Tetrahydronaphthalene |
| 6.8 | 1.47 | Cyclopentanol |

Example 3

Figure 3:
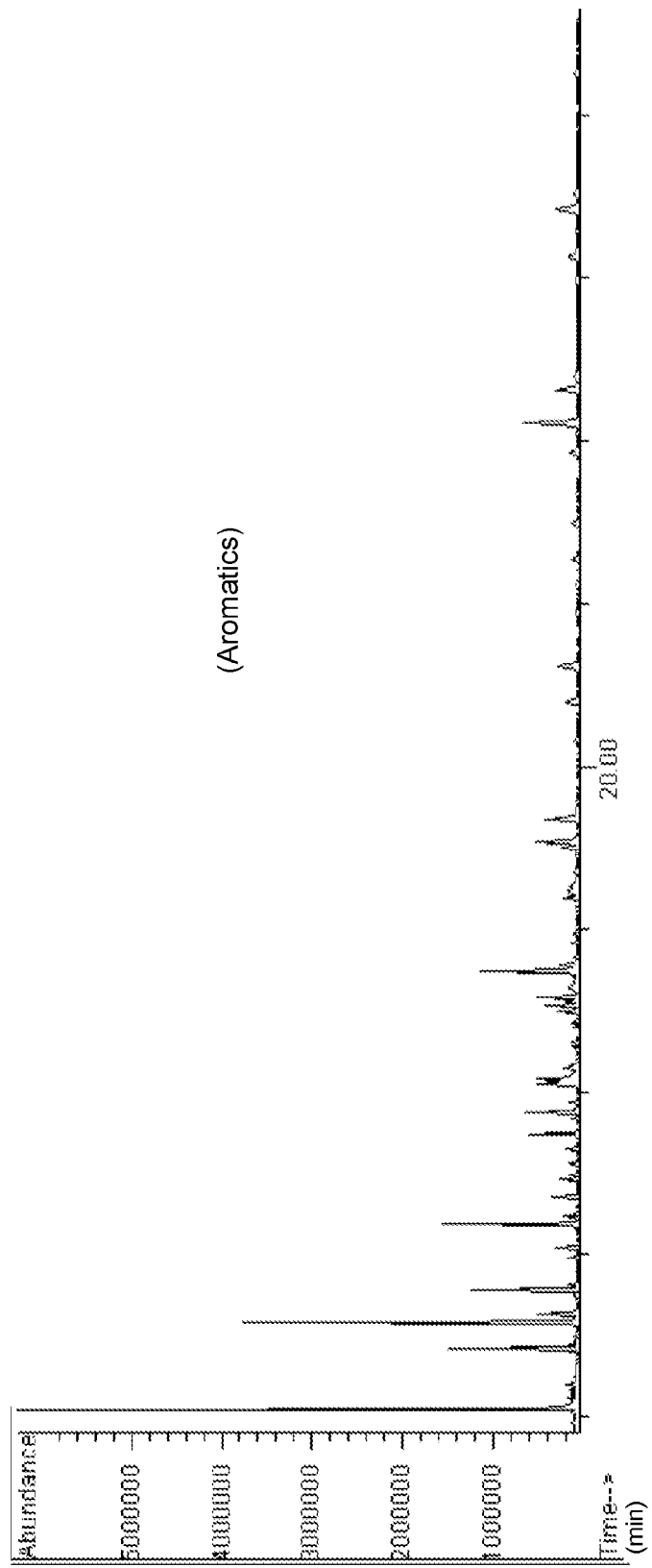
FIG. 3 is a gas chromatograph trace of a converted lignin stream comprising primarily aromatic compounds (reformate).

Conversion of Lignin Feedstream to Aromatics-Rich Converted Lignin Stream 60 grams of ~50% wet lignin feedstream were reacted in the presence of 30 grams of Johnson Mathey A-5000 sponge nickel catalyst (50% by weight water/50% by weight catalyst), 110 grams of DI water and 1 gram of CBV Zeolite catalyst from Zeolyst Corporation. The reactor was pressured to a hydrogen pressure of 52.7 bar at 25° C. Reaction temperature was 350° C., corresponding to an operating pressure in the range of 146-201 bar; reaction time was 1.5 hours. Reaction products were determined according to Procedure N.1. A sample trace of this converted lignin stream is shown in FIG. 3.

TABLE 3

Composition of the aromatics-rich converted lignin stream.

| Retention Time (min) | Area % | Compounds |
|---|---|---|
| 4.2 | 14.68 | Toluene |
| 6.3 | 10.05 | Ethyl benzene |
| 8.7 | 4.34 | Propyl benzene |
| 15.0 | 4.25 | Naphthalene |
| 28.4 | 4.20 | >C15 alkane |
| 5.7 | 3.46 | Ethyl cyclohexane |
| 7.1 | 3.15 | p-Xylene |
| 18.1 | 2.82 | Methyl naphthalene |
| 12.3 | 2.55 | Methyl Indane |
| 33.7 | 2.40 | >C15 alkane |
| 12.2 | 2.24 | Methyl Indane |
| 18.7 | 2.18 | Methyl naphthalene |
| 29.2 | 2.16 | >C15 alkane |
| 11.5 | 2.15 | Butyl benzene |
| 22.5 | 2.09 | >C15 alkane |
| 6.5 | 1.82 | m,o-Xylene |
| 11.0 | 1.79 | Indane |
| 14.3 | 1.65 | Tetrahydronaphthalene |
| 14.5 | 1.60 | Ethyl phenol |

Example 4

Conversion of Lignin Feedstream to
Naphthenes-Rich Converted Lignin Stream 5.25 grams of ~50% wet lignin feedstream were reacted in the presence of 3.75 grams of water, 6.00 grams of Johnson Mathey A-5000 sponge nickel catalyst (50% by weight water/ 50% by weight catalyst) and 0.21 grams of CBV600 Zeolite catalyst from Zeolyst Corporation. The reactor was pressured to a hydrogen pressure of 172 bar at 25° C. Reaction temperature was 305° C. corresponding to an operating pressure in the range of 233-237 bar; reaction time was 3.0 hours.

Figure 2:
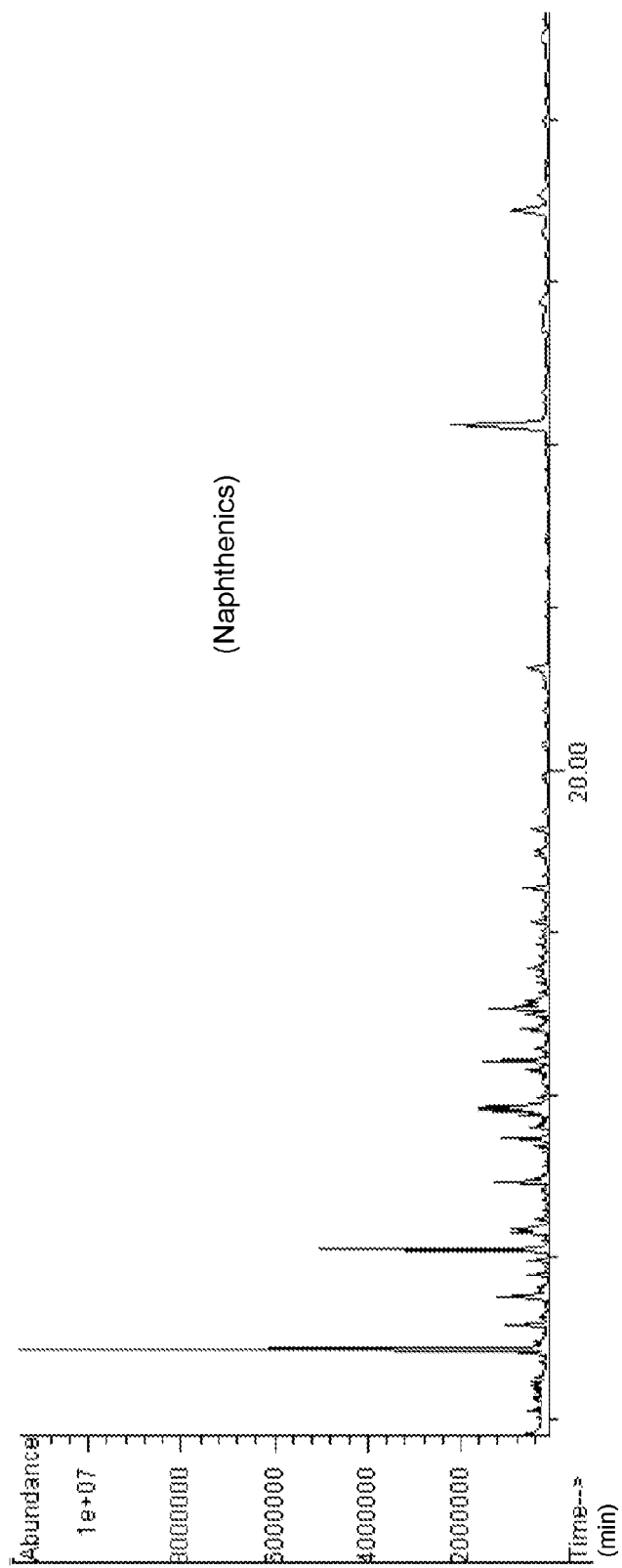
FIG. 2 is a gas chromatograph trace of a converted lignin stream comprising primarily naphthenic compounds.

Reaction products were determined according to Procedure N.1. Composition of reaction products are reported in Table 4. Naphthenic compounds are the major components of the converted lignin feedstream. A sample trace of this converted lignin stream is shown in FIG. 2.

TABLE 4

Composition of the naphthenes-rich converted lignin stream.

| Retention Time (min) | Area % | Compounds |
|---|---|---|
| 5.7 | 16.99 | Ethyl cyclohexane |
| 28.5 | 10.07 | >C15 alkane |
| 11.7 | 8.31 | Ethyl cyclohexanol isomers |
| 8.2 | 7.52 | Propyl cyclohexane |
| 33.8 | 3.70 | >C15 alkane |
| 7.0 | 2.24 | Cyclohexanol |
| 12.9 | 2.13 | Decahydronaphthalene |
| 14.1 | 2.11 | Methyl decahydronaphthalene |
| 8.6 | 2.00 | Methyl cyclohexanol |
| 22.5 | 1.93 | > saturated C12 alkane |
| 8.7 | 1.92 | Methyl cyclohexanol |
| 9.8 | 1.77 | Octahydroindene |
| 18.0 | 1.77 | >C15 alkane |
| 10.9 | 1.48 | Butyl cyclohexane |
| 17.1 | 1.24 | Methyl tetrahydronaphthalene |
| 30.8 | 1.22 | >C15 alkane |
| 11.5 | 1.19 | Ethyl cyclohexanol isomer |
| 6.3 | 1.19 | Ethylbenzene |
| 14.0 | 1.09 | Methy dihydroindene |
| 34.1 | 1.01 | >C15 alkane |

Example 5

Conversion of Lignin Feedstream to Alcohol-Rich
Converted Lignin Stream 5.25 grams of ~50% wet lignin feedstream were reacted in the presence of 3.75 grams of water, 5.98 grams of Johnson Mathey A-5000 sponge nickel catalyst (50% by weight water/ 50% by weight catalyst) and 0.19 grams of CBV600 Zeolite catalyst from Zeolyst Corporation. The reactor was pressured to a hydrogen pressure of 172 bar at 25° C. Reaction temperature was 255° C., corresponding to an operating pressure in the range of 218-230 bar; reaction time was 1.5 hours.

Reaction products were determined according to Procedure N.1. Composition of reaction products are reported in Table 5. Alcohols are the major components of the converted lignin feedstream. A sample trace of this converted lignin stream is shown in FIG. 1.

TABLE 5

Composition of the alcohols-rich converted lignin stream

| Retention Time (min) | Area % | Compounds |
|---|---|---|
| 11.7 | 18.66 | Ethyl cyclohexanol isomers |
| 20.0 | 14.18 | > saturated C12 alkane |
| 7.0 | 10.93 | Cyclohexanol |
| 8.7 | 4.43 | Methyl cyclohexanol |
| 8.6 | 4.34 | Methyl cyclohexanol |
| 28.5 | 3.96 | > saturated C15 alkane |
| 4.6 | 3.65 | Cyclopentanol |
| 5.9 | 3.13 | Methyl cyclopentanol |
| 16.3 | 2.82 | > saturated C10 alcohol |
| 14.1 | 2.41 | >saturated C8 alcohol |
| 11.5 | 2.14 | Ethyl cyclohexanol isomers |
| 5.7 | 2.09 | Ethyl cyclohexane |
| 17.2 | 1.87 | 4-Ethyl,2-methoxyphenol |

In Table 6 the results of presented experiments are summarized.

It has to be pointed out that the operating pressure varies during reaction evolution.

TABLE 6

Experimental results summary

| Experiment | Hydrogen pressure at 25° C. (bar) | Reaction temperature (° C.) | Reaction time (h) | Main products |
|---|---|---|---|---|
| Example 1 | 77.5 | 350 | 1.5 | None/unreacted |
| Example 2 | 13.8 | 305 | 1.0 | phenols |
| Example 3 | 52.7 | 350 | 1.5 | aromatics |
| Example 4 | 172 | 305 | 3 | naphthenes |
| Example 5 | 172 | 255 | 1.5 | alcohols |

Composition Determination Standard Analytical Methods Used for Composition Determination Compositions were performed according to the following NREL standards NREL Analytical Method Determination of Structural Carbohydrates and Lignin in Biomass Laboratory Analytical Procedure (LAP) Issue Date: Apr. 25, 2008

*Technical Report* NREL/TP-510-42618 Revised April 2008

Determination of Extractives in Biomass

Laboratory Analytical Procedure (LAP) Issue Date: Jul. 17, 2005

*Technical Report* NREL/TP-510-42619 January 2008
Preparation of Samples for Compositional Analysis
Laboratory Analytical Procedure (LAP) Issue Date: Sep. 28, 2005

*Technical Report* NREL/TP-510-42620 January 2008
Determination of Total Solids in Biomass and Total Dissolved Solids in Liquid Process Samples
Laboratory Analytical Procedure (LAP) Issue Date: Mar. 31, 2008

*Technical Report* NREL/TP-510-42621 Revised March 2008
Determination of Ash in Biomass
Laboratory Analytical Procedure (LAP) Issue Date: Jul. 17, 2005

*Technical Report* NREL/TP-510-42622 January 2008
Determination of Sugars, Byproducts, and Degradation Products in Liquid Fraction Process Samples
Laboratory Analytical Procedure (LAP) Issue Date: Dec. 8, 2006

*Technical Report* NREL/TP-510-42623 January 2008
Determination of Insoluble Solids in Pretreated Biomass Material
Laboratory Analytical Procedure (LAP) Issue Date: Mar. 21, 2008

NREL/TP-510-42627 March 2008

We claim:

1. A process for the one-step conversion of a pre-treated lignin feedstream that has been pre-treated by steam explosion, hydrolysis, and fermentation into a converted lignin stream, the process comprised of:
    combining in a lignin conversion vessel: the pre-treated lignin feedstream, water supplied from the group consisting of the pre-treated lignin feedstream, a source other than the pre-treated lignin feedstream and mixtures thereof, hydrogen having a hydrogen pressure which at 25° C. is in the range of 35 to 138.9 bar, and a first catalyst comprising an elemental metal catalyst, and
    maintaining the combination in the lignin conversion vessel at a first temperature in the range of 320° C. to 360° C. for a time sufficient to create the converted lignin stream,
    wherein the pre-treated lignin feedstream comprises lignin, cellulose and water wherein the ratio of moles of hydrogen to moles of lignin and cellulose is at least 0.5 and wherein the lignin of the pre-treated lignin feedstream is present as a solid.

2. The process according to claim 1, wherein the first catalyst comprises an elemental metal selected from the group consisting of Platinum, Palladium, Cesium, Copper, Nickel, Ruthenium, Rhodium, Gold, and Iridium.

3. The process according to claim 1, wherein the weight of the first catalyst to the dry weight of the pre-treated lignin feedstream is in the range of about 0.005 to about 2.0.

4. The process according to claim 1, wherein first catalyst is a bimetallic catalyst comprised of at least one metal selected from the group consisting of Platinum, Palladium, Cesium, Copper, Nickel, Ruthenium, Rhodium, Gold and Iridium.

5. The process according to claim 1, wherein the lignin conversion further occurs in the presence of a second catalyst wherein the second catalyst is a zeolite.

6. The process according to claim 1, wherein the first catalyst is selected from the group consisting of Nickel Catalysts, Raney Nickel catalysts, Ruthenium containing catalysts, Rhodium containing catalysts, Copper containing catalysts, Palladium containing catalysts, Cesium containing catalysts, Gold containing catalysts, Iridium containing catalysts and Platinum containing catalysts.

* * * * *